United States Patent
McClements et al.

(10) Patent No.: US 9,040,109 B2
(45) Date of Patent: May 26, 2015

(54) CROSS-LINKED BIOPOLYMERS, RELATED COMPOSITIONS AND METHODS OF USE

(71) Applicants: David Julian McClements, Northampton, MA (US); Eric Andrew Decker, Sunderland, MA (US)

(72) Inventors: David Julian McClements, Northampton, MA (US); Eric Andrew Decker, Sunderland, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/085,212

(22) Filed: Nov. 20, 2013

(65) Prior Publication Data

US 2014/0079816 A1  Mar. 20, 2014

Related U.S. Application Data

(62) Division of application No. 12/809,185, filed as application No. PCT/US2008/013979 on Dec. 22, 2008, now Pat. No. 8,603,566.

(60) Provisional application No. 61/008,389, filed on Dec. 20, 2007.

(51) Int. Cl.
| A23D 7/00 | (2006.01) |
| A61K 47/48 | (2006.01) |
| A61K 9/00 | (2006.01) |
| A61K 9/107 | (2006.01) |
| A23D 7/005 | (2006.01) |
| A23D 7/02 | (2006.01) |
| A61K 8/06 | (2006.01) |
| A61K 33/00 | (2006.01) |

(52) U.S. Cl.
CPC .............. *A61K 9/107* (2013.01); *A23D 7/0053* (2013.01); *A23D 7/02* (2013.01); *A61K 8/062* (2013.01); *A61K 33/00* (2013.01)

(58) Field of Classification Search
CPC ....... A23D 7/0053; A23D 7/02; A61K 33/00; A61K 8/062; A61K 9/107
See application file for complete search history.

(56) References Cited

U.S. PATENT DOCUMENTS

| 7,052,729 B2 | 5/2006 | Antheunisse et al. |
| 8,137,728 B2 | 3/2012 | McClements et al. |
| 2005/0202149 A1 | 9/2005 | McClements et al. |

FOREIGN PATENT DOCUMENTS

WO  2006016809 A1  2/2006

OTHER PUBLICATIONS

Littoz, F. et al. Bio-mimetic approach to improving emulsion stability: Cross-linking adsorbed beet pectin layers using laccase. Food Hydrocolloids 22 (2008), pp. 1203-1211.
Genipin. Myria Screen, Diversity Collection. http://www.timetec.net/genipin.html. Copyright 2008.
Surh, J. et al. Preparation and Characterization of Water/Oil and Water/Oil/Water Emulsions Containing Biopolymer-Gelled Water Droplets. J. Agric. Food Chem. 2007, vol. 55, No. 1, pp. 175-184.

*Primary Examiner* — Abigail Fisher
(74) *Attorney, Agent, or Firm* — Bruns & Levinson LLP; Orlando Lopez

(57) ABSTRACT

The present invention provides stabilized oil-in-water emulsions with an extended range of chemical, thermal and/or mechanical stabilities, and method(s) for their preparation. Such preparations provide an environmentally-protective biopolymer component exhibiting improved adherence to the dispersed phase, reducing or eliminating dissociation therefrom under such conditions, for use in the context of a range of food, pharmaceutical, personal care, health care, cosmetic and other end-use applications.

19 Claims, 10 Drawing Sheets

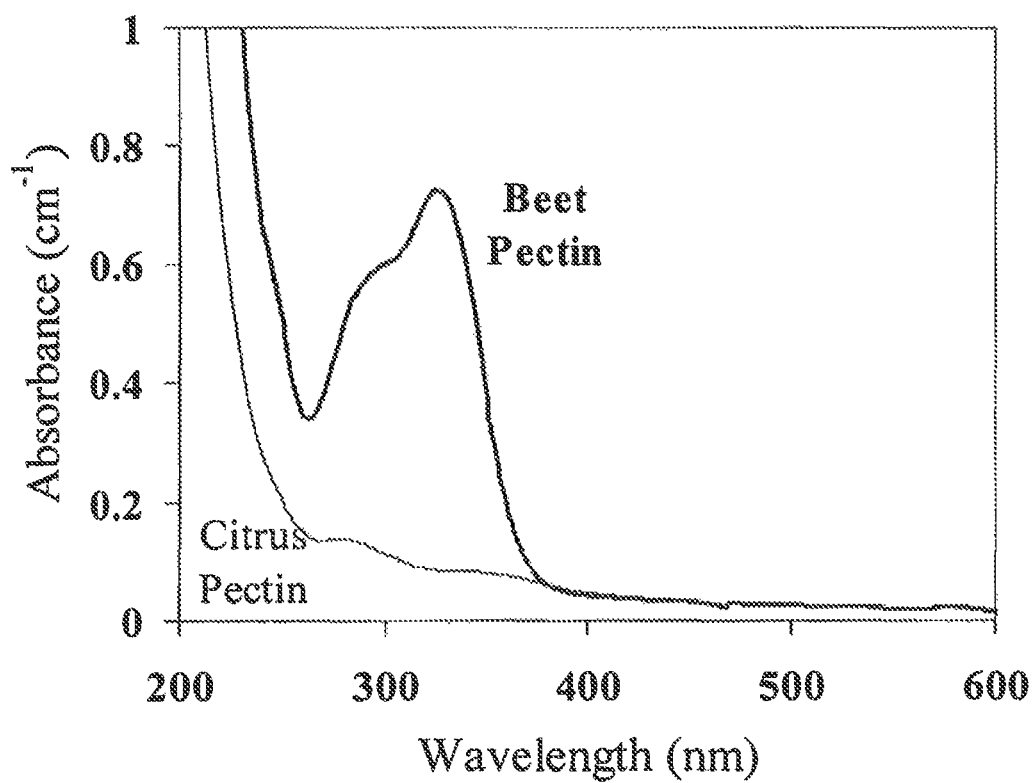

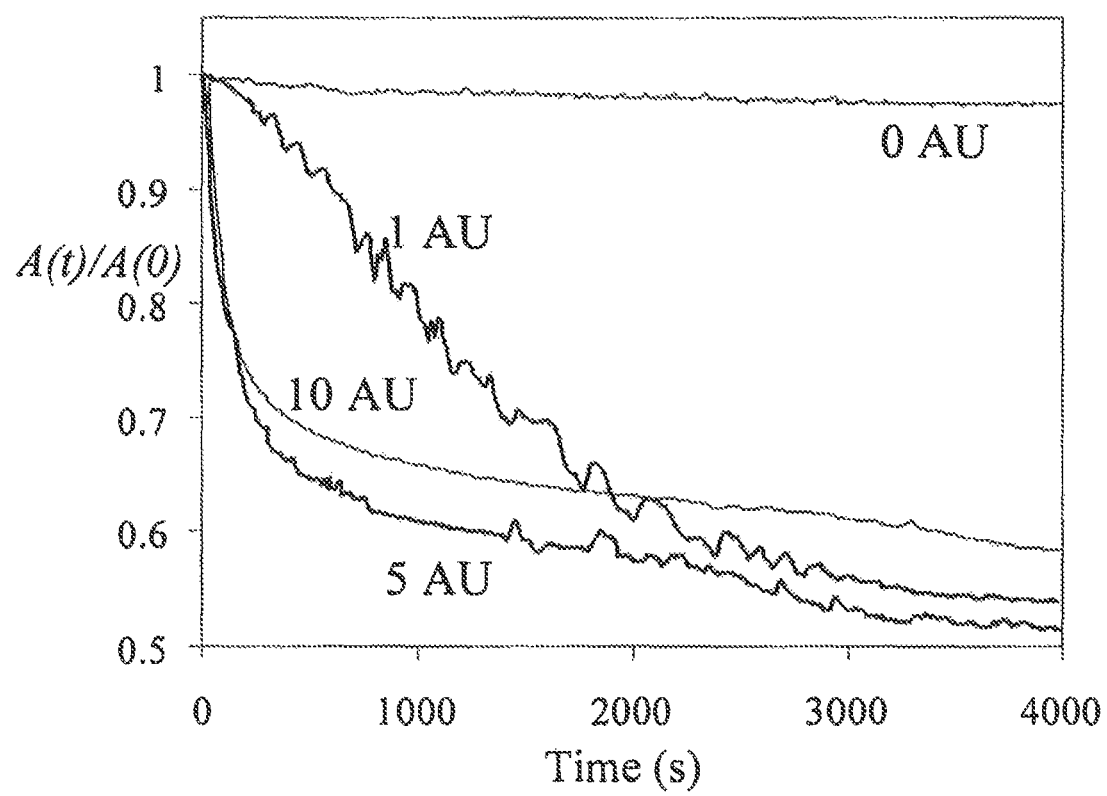

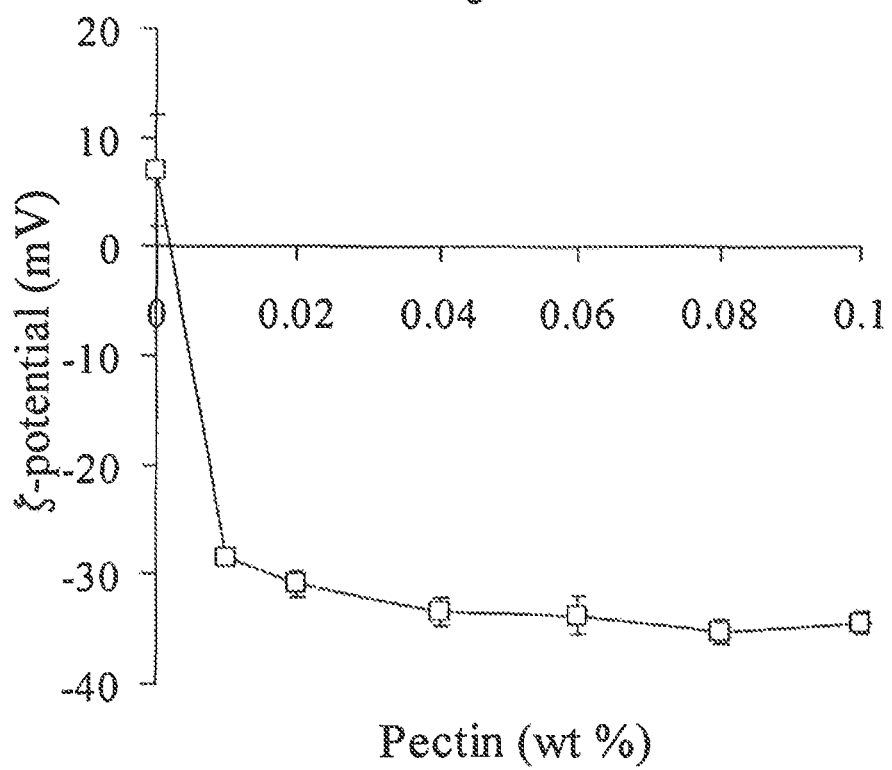

CROSS-LINKED BIOPOLYMERS, RELATED COMPOSITIONS AND METHODS OF USE

Figure 2B:
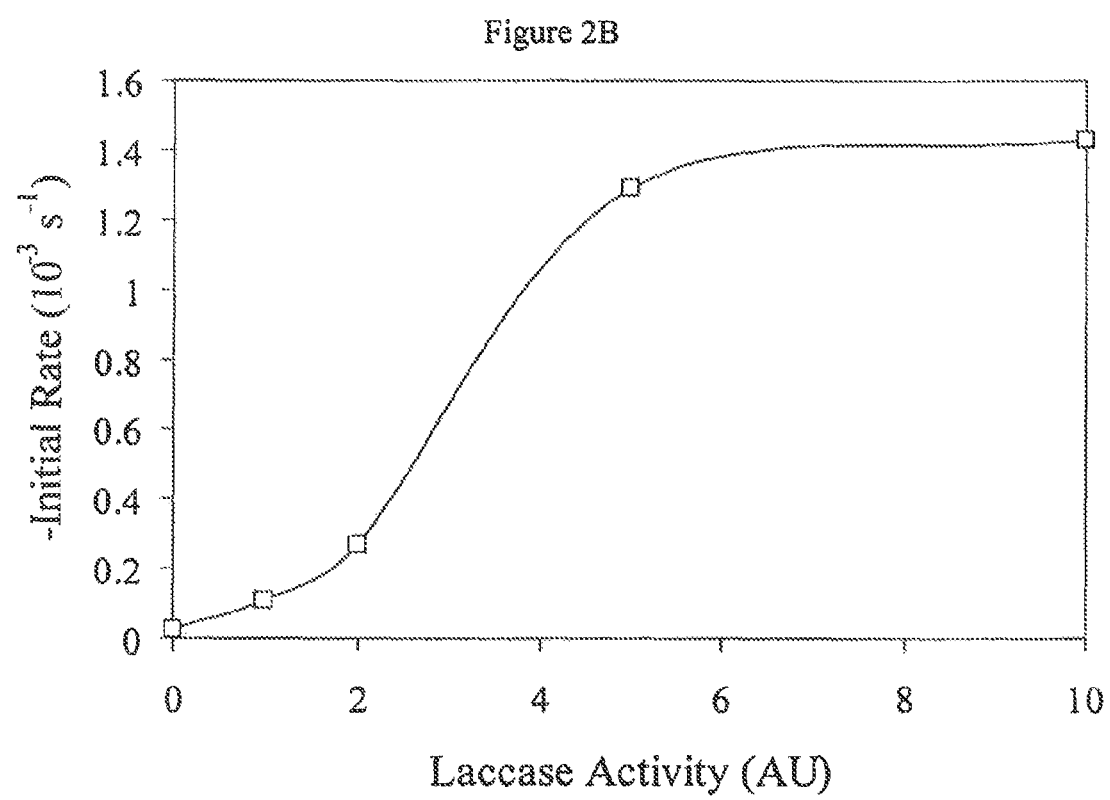

This application is division of co-pending U.S. patent application Ser. No. 12/809,185 which in turn is a U.S. national stage application under 35 U.S.C. 371 of International Application No. PCT/US08/13979 filed Dec. 22, 2008 and entitled CROSS-LINKED BIOPOLYMERS. RELATED COMPOSITIONS AND METHODS OF USE, which in turn claims priority benefit of Provisional Application No. 61/008,389 filed Dec. 20, 2007, the entirety of which is incorporated herein by reference for all purposes.

The United States government has certain rights to this invention pursuant to Award Nos. 2002-35503-12296 and 2005-35503-16164 from the United States Department of Agriculture to the University of Massachusetts.

BACKGROUND OF THE INVENTION

Protein-stabilized oil-in-water emulsions are widely utilized in the food, cosmetics and pharmaceutical industries. These emulsions consist of protein-coated lipid droplets dispersed in an aqueous continuum. Conventionally, these emulsions are created by homogenizing an oil phase with an aqueous phase containing surface-active proteins, such as to casein, soy proteins, egg proteins or whey proteins. The protein molecules adsorb to the surface of the droplets produced during homogenization where they form a protective coating that prevents them from aggregating, e.g., flocculating and/or coalescing. In addition, the adsorbed proteins reduce the oil-water interfacial tension, thereby facilitating the further disruption of lipid droplets during homogenization and leading to smaller droplet sizes. At present, proteins can only be used successfully as emulsifiers in a limited range of materials because of their high sensitivity to changes in solution pH and ionic strength. Protein-coated lipid droplets are primarily stabilized by electrostatic repulsion, consequently they tend to aggregate when the pH moves close to the isoelectric point of the proteins (due to reduction of the ζ-potential) or when the ionic strength increases above a certain level (due to increased electrostatic screening). In addition, protein-coated lipid droplets are often susceptible to aggregation when they are heated above the thermal denaturation temperature of the adsorbed proteins because this increases the hydrophobic attraction between them.

Recently, an interfacial engineering technology, based on the layer-by-layer (LbL) electrostatic deposition technique, has been used to improve the stability of protein-coated lipid droplets to environmental stresses, such as pH, ionic strength and temperature. Initially, a "primary emulsion" consisting of lipid droplets coated by a layer of charged globular proteins is produced using conventional homogenization. Then, a "secondary emulsion" is formed by depositing an oppositely charged polyelectrolyte (e.g., an ionic polysaccharide) onto the surface of the protein-coated lipid droplets. This procedure can be repeated a number of times by successively depositing layers of oppositely charged polyelectrolytes onto the surfaces of the lipid droplets so that multilayered interfacial coatings are formed. Rational selection of polyelectrolyte characteristics and deposition conditions enables one to carefully control interfacial characteristics, such as thickness, charge, permeability, environmental responsiveness and functionality.

One potential limitation of the electrostatic deposition method for certain applications is that interfacial protein-polysaccharide complexes are only held together by electrostatic attraction. Consequently, the polysaccharide layer may dissociate from the protein-coated lipid droplet surfaces when the pH is varied so that the protein and polysaccharide have opposite charges, or when the ionic strength is increased above a certain level. As a result, there remains an on-going search in the art to provide emulsion systems that remain intact with changes in pH or ionic strength of the surrounding solution.

SUMMARY OF THE INVENTION

In light of the foregoing, it is an object of the present invention to provide stabilized oil-in-water emulsions and method(s) for their preparation, thereby overcoming various deficiencies of the prior art including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to enhance the physical stability of such emulsions to environmental stresses.

It can be another object of the present invention to extend the range of chemical, thermal and/or mechanical conditions over which such emulsions can be utilized without either degradation or aggregation.

It can be another object of the present invention to provide an environmentally-protective biopolymer component exhibiting improved adherence to the dispersed phase, reducing or eliminating dissociation therefrom under such conditions.

It can also be an object of the present invention, alone or in conjunction with one or more of the preceding objectives, to provide stabilized oil-in-water emulsions and/or methods for their preparation, for use in the context of a range of food, pharmaceutical, personal care, health care, cosmetic and/or other end-use applications.

Other objects, features, benefits and advantages of the present invention will be apparent from this summary and the following descriptions of certain embodiments, and will be readily apparent to those skilled in the art having knowledge of such emulsions, related processes and applications. Such objects, features, benefits and advantages will be apparent from the above as taken into conjunction with the accompanying examples, data, figures and all reasonable inferences to be drawn therefrom.

In part, the present invention can be directed to a composition comprising a hydrophobic fat/oil component; an emulsifier component about the hydrophobic component; and a biopolymer component adsorbed on, electrostatically, interactive with and/or coupled to the hydrophobic component and/or the emulsifier component, such a biopolymer component comprising an intra-component covalent cross-linkage, such a linkage as can be considered the reaction product of cross-linkable moieties and a cross-linking agent/reagent.

Without limitation, a hydrophobic component of such embodiments can be at least partially insoluble in an aqueous or another medium and/or is capable of forming emulsions in an aqueous medium. In certain such embodiments, a hydrophobic component can comprise a fat, an oil or a component thereof, including but not limited to any edible food oil known to those skilled in the art (e.g., without limitation, corn, soybean, canola, rapeseed, olive, peanut, algal, palm, coconut, nut and/or vegetable oils, fish oils or combinations thereof). A hydrophobic component can be selected from hydrogenated or partially hydrogenated fats and/or oils, and can include any dairy or animal fat or oil including, for example, dairy fats. In addition, the hydrophobic component can further comprise flavors, antioxidants, nutrients, nutraceuticals, preservatives and/or nutritional components, such as fat soluble vitamins.

It will be readily apparent that, consistent with the broader aspects of the invention, a hydrophobic component can further include any natural and/or synthetic lipid components including, but not limited to, fatty acids (saturated or unsaturated), glycerols, glycerides and their respective derivatives, phospholipids and their respective derivatives, glycolipids, phytosterol and/or sterol esters (e.g., cholesterol esters, phytosterol esters and derivatives thereof), carotenoids, terpenes, antioxidants, colorants, and/or flavor oils (for example, peppermint, citrus, coconut, or vanilla and extracts thereof such as terpenes from citrus oils), as may be required by a given food or beverage end use application. Other such components include, without limitation, brominated vegetable oils, ester gums, sucrose acetate isobutyrate, damar gum and the like. The present invention, therefore, contemplates a wide range of edible oil/fat, waxes and/or lipid components of varying molecular weight and comprising a range of hydrocarbon (aromatic, saturated or unsaturated), alcohol, aldehyde, ketone, acid and/or amine moieties or functional groups.

An emulsifier component can comprise any food-grade surface active ingredient, cationic surfactant, anionic surfactant and/or amphiphilic surfactant known to those skilled in the art capable of at least partly emulsifying the hydrophobic component in an aqueous medium and imparting a net charge to at least a portion thereof. Accordingly, such an emulsifier component can be selected from one or more small-molecule surfactants, fatty acids, phospholipids, proteins and polysaccharides, and derivatives thereof. Such emulsifiers can further include one or more of, but not limited to, lecithin, chitosan, modified starches, pectin, gums (e.g., locust bean gum, gum arabic, guar gum, etc.), alginic acids, alginates and derivatives thereof, and cellulose and derivatives thereof. Protein emulsifiers can include any one of the dairy proteins (e.g., without limitation, whey and casein), vegetable proteins (e.g., soy), meat proteins, fish proteins, plant proteins, egg proteins, ovalbumins, glycoproteins, mucoproteins, phosphoproteins, serum albumins, collagen and combinations thereof. Protein emulsifying components can be selected on the basis of their amino acid residues (e.g., lysine, arginine, aspartic acid, glutamic acid, etc.) to optimize the overall net charge of the interfacial membrane about the hydrophobic component, and therefore the stability of the hydrophobic component within an emulsion system.

Indeed, an emulsifier component can include a broad spectrum of emulsifiers including, for example, acetic acid esters of monogylcerides (ACTEM), lactic acid esters of monogylcerides (LACTEM), citric acid esters of monogylcerides (CITREM), diacetyl acid esters of monogylcerides (DATEM), succinic acid esters of monogylcerides, polyglycerol polyricinoleate, sorbitan esters of fatty acids, propylene glycol esters of fatty acids, sucrose esters of fatty acids, mono and diglycerides, fruit acid esters, stearoyl lactylates, polysorbates, starches, sodium dodecyl sulfate (SDS) and/or combinations thereof.

Regardless, a biopolymer component can comprise any food-grade polymeric material capable of adsorption on, electrostatic interaction with and/or coupling to a hydrophobic component and/or an associated emulsifier component. Accordingly, such a biopolymer component can be selected from one or more proteins, one or more polysaccharides and combinations thereof. Without limitation, such a biopolymer component can be selected from but not limited to food-grade ionic or ionizable proteins such as whey, casein, soy, egg, plant, meat and fish proteins, ovalbumins, glycoproteins, mucoproteins, phosphoproteins, serum albumins and collagens, and ionic or ionizable polysaccharides such as chitosan and/or chitosan sulfate, cellulose, pectins, alginic acids, alginates, glycogen, amylose, chitin, gum arabic, gum acacia, carageenans, xanthans, agars, tree gums and exudates thereof, guar gum, gellan gum, tragacanth gum, karaya gum, locust bean gum, lignin, nucleic acids, polynucleotides and/or combinations thereof. As mentioned above, such protein components can be selected on the basis of their amino acid residues (e.g., lysine, arginine, aspartic acid, glutamic acid, etc.) to optimize overall net charge, interaction with an emulsifier component and/or resultant emulsion stability. The food-grade polymeric component may alternatively be selected from modified polymers such as modified starch, modified celluloses, carboxymethyl cellulose, carboxymethyl dextran or lignin sulfonates.

As mentioned above and described elsewhere herein, such a biopolymer—regardless of specific composition—can comprise covalent intra-component cross-linkages, as would be understood by those skilled in the art made aware of this invention. Such intra-component structures can be achieved by introduction of and/or use of an agent or reagent at least partially sufficient to at least partially cross-link the biopolymer component(s). Such agents are as would be understood by those skilled in the art and include, without limitation, compounds, enzymes, heat, pH, and various redox reagents. In certain such embodiments, depending upon choice of biopolymer component and cross-linkable moiety or moieties present therewith, enzymatic cross-linking can be employed. Without limitation, various pectins can be, as described below, cross-linked by the activity of laccase and peroxidase enzymes.

In certain embodiments of this invention, an emulsifier component—depending upon the presence of one or more cross-linkable moieties—can also be covalently cross-linked under applicable reaction or process conditions employed. Without limitation, various whey proteins can also be enzymatically cross-linked. Accordingly, in certain such compositional embodiments of this invention, the emulsifier and biopolymer components can be covalently cross-linked, such cross-linkages selected from covalent intra-component cross-linkages, covalent inter-component cross-linkages and combinations thereof.

The present invention contemplates any combination of emulsifier and biopolymer components leading to the formation of a multi-layered composition comprising an oil/fat and/or lipid hydrophobic component sufficiently stable under environmental or end-use conditions (e.g., as applicable to a particular food product). Accordingly, a hydrophobic component can be at least partially coated or encapsulated with and/or immobilized by a wide range of emulsifiers/polymeric components, depending upon the pH, ionic strength, salt concentration, temperature and processing requirements of the system/food product into which a hydrophobic component is to be incorporated. Such an emulsifier/biopolymer component combinations are limited only by interaction one with another and covalent intra- and/or inter-component cross-linking thereof.

As illustrated herein, such compositions can be provided in the context of an emulsion system: for example, as a dispersed phase in an aqueous continuous phase. The resulting emulsion compositions/products can be dehydrated (e.g., by spray- or freeze-drying), then reconstituted for later use. Regardless, one or more such cross-linked compositions can be employed with a range of end-use applications including but limited to foods, beverages, pharmaceuticals, nutraceuticals, personal and health care products, agro-chemicals, cosmetics and the like.

In part, this invention can provide a biomimetic method for preparation and/or stabilizing an emulsified substantially hydrophobic oil/fat component. Such a method can comprise providing a hydrophobic and/or oil/fat and/or lipid component; contacting the hydrophobic/oil/fat component with one or more emulsifier components, at least a portion of each as can comprise a net charge; contacting or incorporating therewith one or more food-grade biopolymer components can comprise a cross-linkable moiety, at least a portion of each as can comprise a net charge opposite that of the emulsifier component and/or a previously incorporated food-grade polymeric component; and introduction of an agent at least partially sufficient to at least partially covalently cross-link the biopolymer component(s). Hydrophobic, emulsifier and biopolymer components can be as known to those skilled in the art made aware of this invention and/or selected as described above. In certain embodiments, such a method can comprise alternating contact or incorporation of oppositely charged emulsifier and/or food-grade biopolymer components, each such contact or incorporation comprising electrostatic interaction with a previously contacted or incorporated emulsifier or biopolymer component(s).

Regardless, cross-linking can be achieved by introduction of an agent including but not limited to an enzyme, compound, heat and/or pH and/or hydrogen ion concentration and various redox reagents, depending upon the identity of any cross-linkable moiety present. In certain embodiments, without limitation, a biopolymer component can be a polysaccharide including but not limited to those selected from various available pectins comprising ferulic acid moieties. In certain such embodiments, such biopolymer components can cross-linked by introduction and activity of laccase and/or peroxidase enzymes thereon. In certain other embodiments, an emulsifier component—depending upon the presence of one or more cross-linkable moieties—can also be covalently cross-linked. Without limitation, such an emulsifier component can be selected from various available whey proteins comprising phenolic acid moieties. Introduction and activity of laccase and/or peroxidase enzymes thereon can cross-link the corresponding whey protein. Accordingly, as discussed above, depending upon reaction or process conditions employed, the emulsifier and biopolymer components can be covalently cross-linked, such cross-linking selected from covalent intra-component cross-linking, covalent inter-component cross-linking and combinations thereof.

As illustrated herein, such preparation and/or cross-linking can be in an aqueous continuous phase. The resulting emulsion can be isolated, processed and/or incorporated into a range of food products, beverages, pharmaceuticals, nutraceuticals, personal and health care products, agro-chemicals, cosmetics and various other end-use applications, as would be understood by those skilled in the art made aware of this invention.

In part, this invention can comprise an alternate method for emulsion and particulate formation. With reference to the preceding, a biopolymer component can be incorporated with or contact a composition comprising an oil/fat component and an emulsifier component under conditions or at a pH not conducive for sufficient electrostatic interaction therewith. The pH can then be varied to change the net electrical charge of the emulsion, of the emulsified oil/fat/lipid component and/or of the polymeric component, sufficient to promote electrostatic interaction with and incorporation of the polymeric component. Without limitation, a stable emulsion can be prepared using a protein emulsifier (e.g., without limitation casein, whey, soy, egg or gelatin) at a pH below its isoelectric point, to form cationic or net positively-charged emulsion droplets, then using an anionic or net negatively-charged polysaccharide (e.g., without limitation, a pectin, carrageenan, alginate, or gum arabic) for electrostatic interaction with the initial emulsion composition. Regardless of method of preparation, such emulsions are stable to interaction with other emulsion components or with respect to factors (e.g., pH, ionic strength, temperature, etc.) relating to end-use applications.

Without limitation, with reference to the following examples, emulsions can be prepared using food-grade components and standard preparation procedures (e.g., homogenization and mixing). Initially, a primary aqueous emulsion comprising an electrically charged emulsifier component can be prepared by homogenizing an oil/fat component, an aqueous phase and a suitable emulsifier comprising a net charge. Optionally, mechanical agitation or sonication can be applied to such a primary emulsion to disrupt any floc formation, and emulsion washing can be used to remove any non-incorporated emulsifier component. A secondary emulsion can be prepared by contacting a net-charged biopolymer component with a primary emulsion. The polymeric component can have a net electrical charge opposite to at least a portion of the primary emulsion. Optionally, mechanical agitation or sonication can also be applied to disrupt any floc formation, and emulsion washing can be used to remove any non-incorporated emulsifier component. As discussed above, emulsion characteristics can be altered by pH adjustment to promote or enhance electrostatic interaction of a primary emulsion and a biopolymer component.

DETAILED DESCRIPTION OF THE DRAWINGS

FIG. 1. UV-visible absorption spectra of citrus and beet pectin (0.1 wt %) dissolved in aqueous phosphate buffer solution (5 mM buffer, pH 4.5).

FIGS. 2A-B. Influence of laccase concentration (0 to 10 AU) on (A) the time-dependence of the UV-visible absorbance at 325 nm and (B) the initial slope $(1/A(0) \times dA(t)/dt)$ for beet pectin (0.1 wt %) dissolved in aqueous phosphate buffer solution (5 mM buffer, pH 4.5).

FIG. 3. Dependence of particle charge ($\xi$-potential) on beet pectin concentration for secondary emulsions: 1 wt % corn oil, 0.05 wt % β-Lg, 0 to 0.1 wt % pectin, 5 mM phosphate, pH 4.5.

Figure 4:
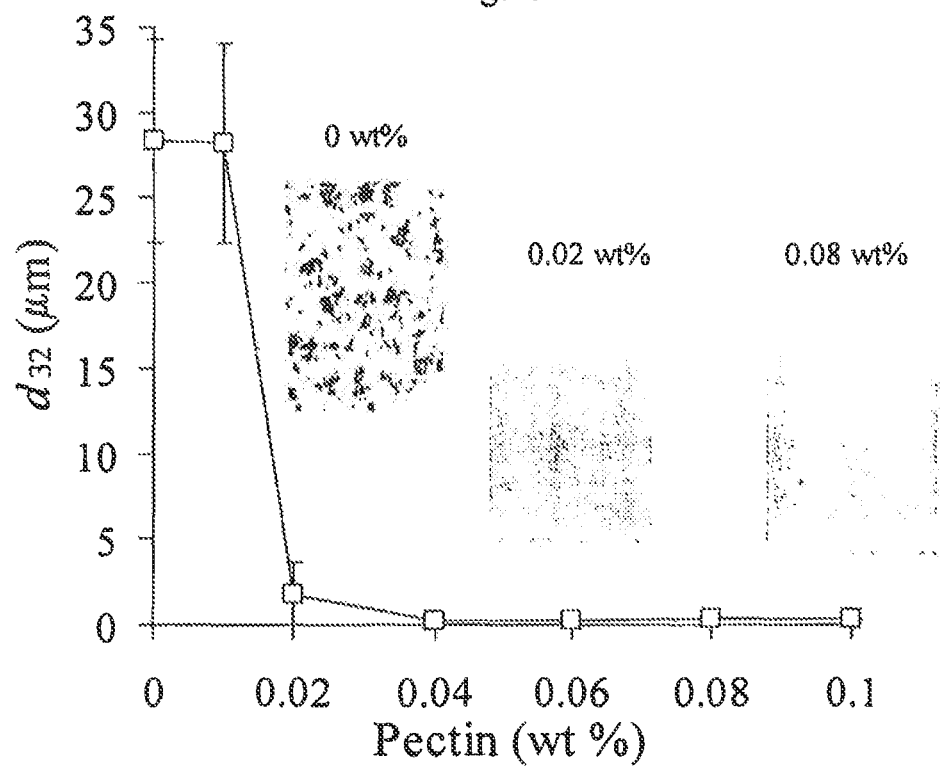

FIG. 4. Dependence of mean particle diameter ($d_{32}$) on beet pectin concentration for secondary emulsions: 1 wt % corn oil, 0.05 wt % β-Lg, 0 to 0.1 wt % pectin, 5 mM phosphate buffer, pH 4.5.

Figure 5:
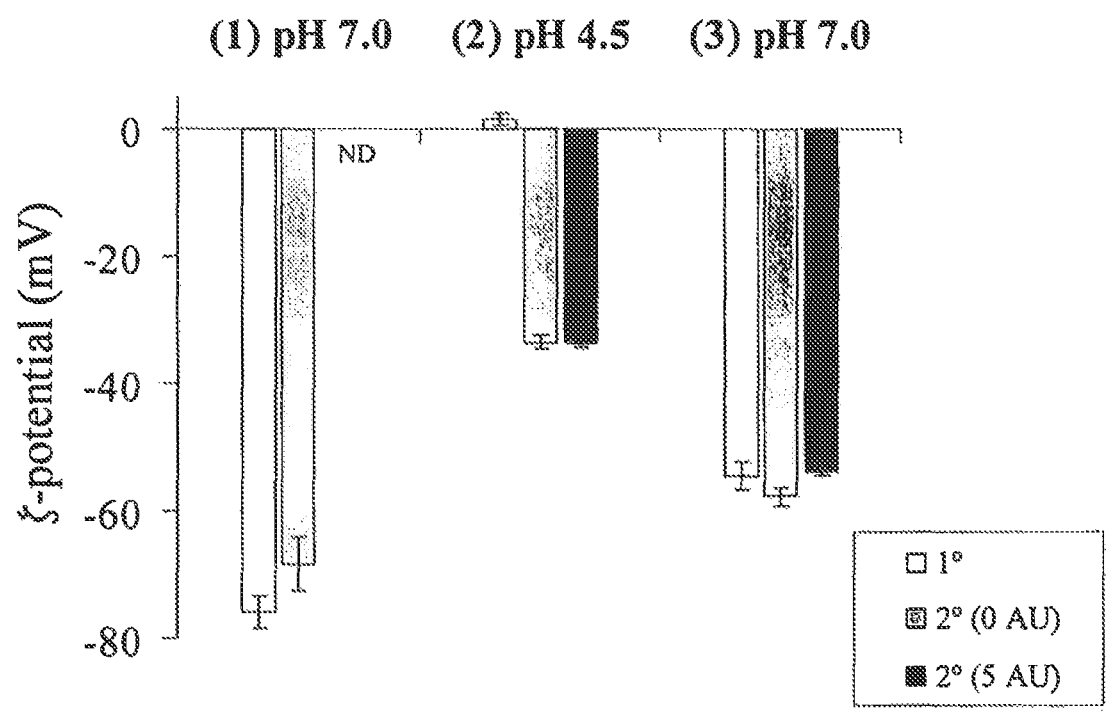

FIG. 5. Dependence of $\zeta$-potential on pH and laccase concentration (0 or 5 AU) for primary and secondary emulsions: 1 wt % corn oil, 0.05 wt % β-Lg, 0 or 0.04 wt % pectin, 5 mM phosphate buffer. The pH of the emulsions was sequentially adjusted from (1) pH 7 to (2) pH 4.5 to (3) pH 7.

Figure 6:
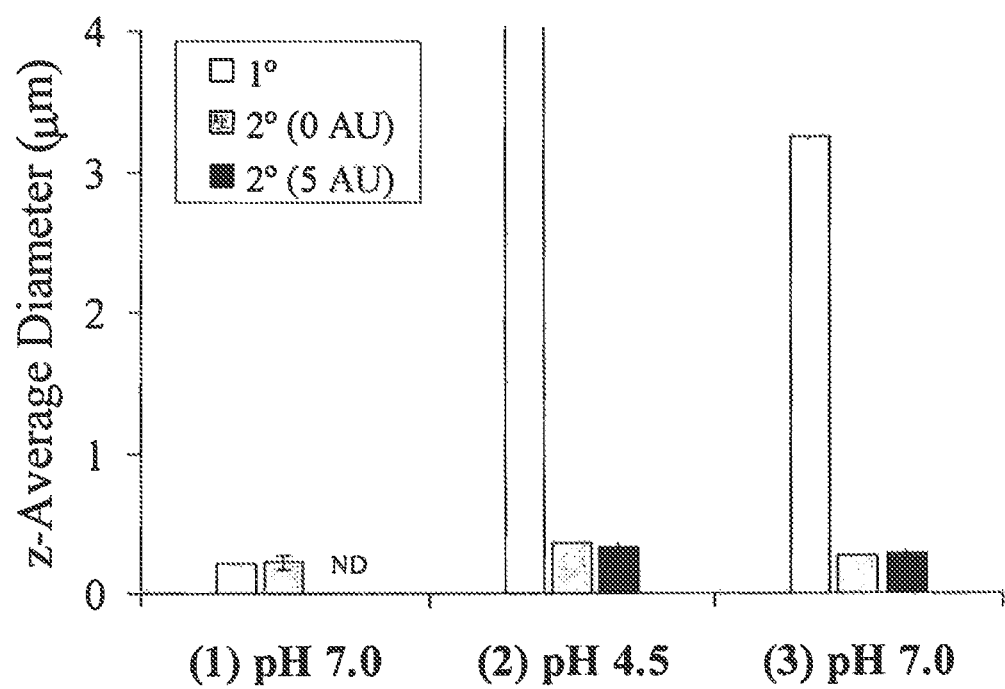

FIG. 6. Dependence of mean particle diameter (z-average) on pH and laccase concentration (0 or 5 AU) for primary and secondary emulsions: 1 wt % corn oil, 0.05 wt % β-Lg, 0 or 0.04 wt % pectin, 5 mM phosphate buffer. The pH of the emulsions was sequentially adjusted from (1) pH 7 to (2) pH 4.5 to (3) pH 7.

Figure 7A:
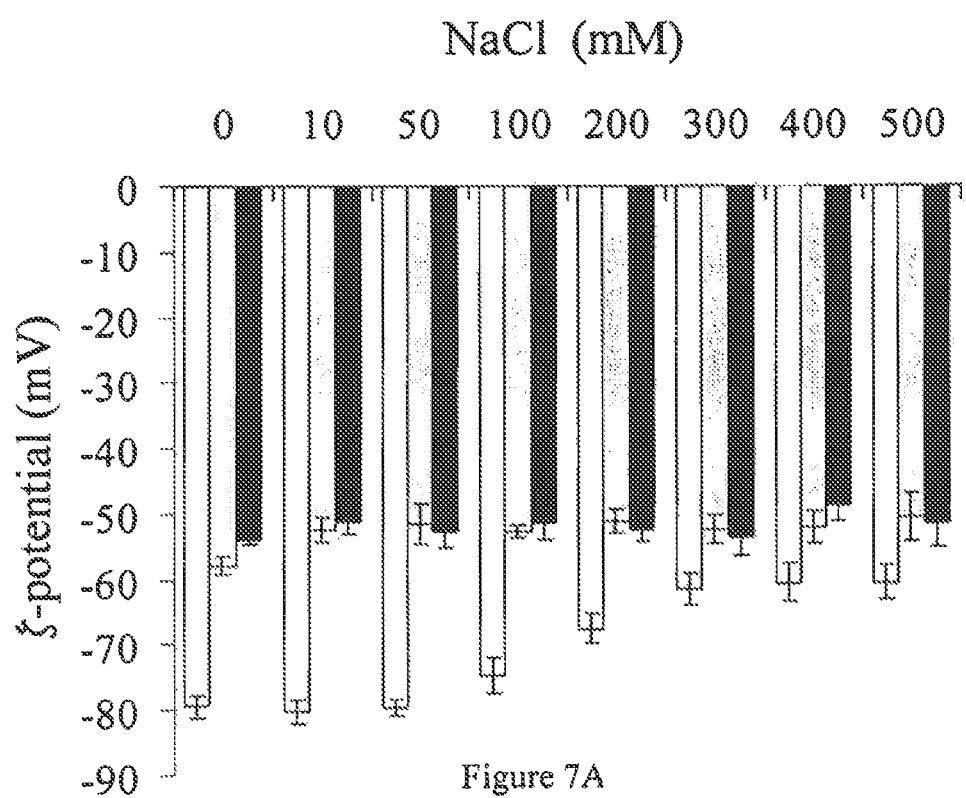
Figure 7B:
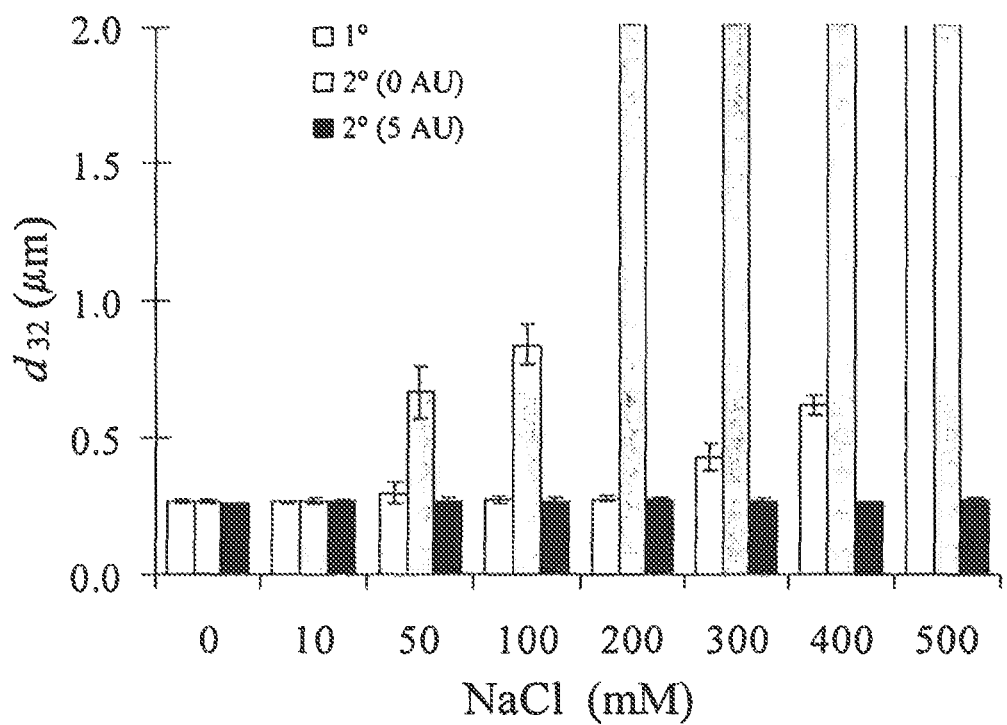
Figure 7C:
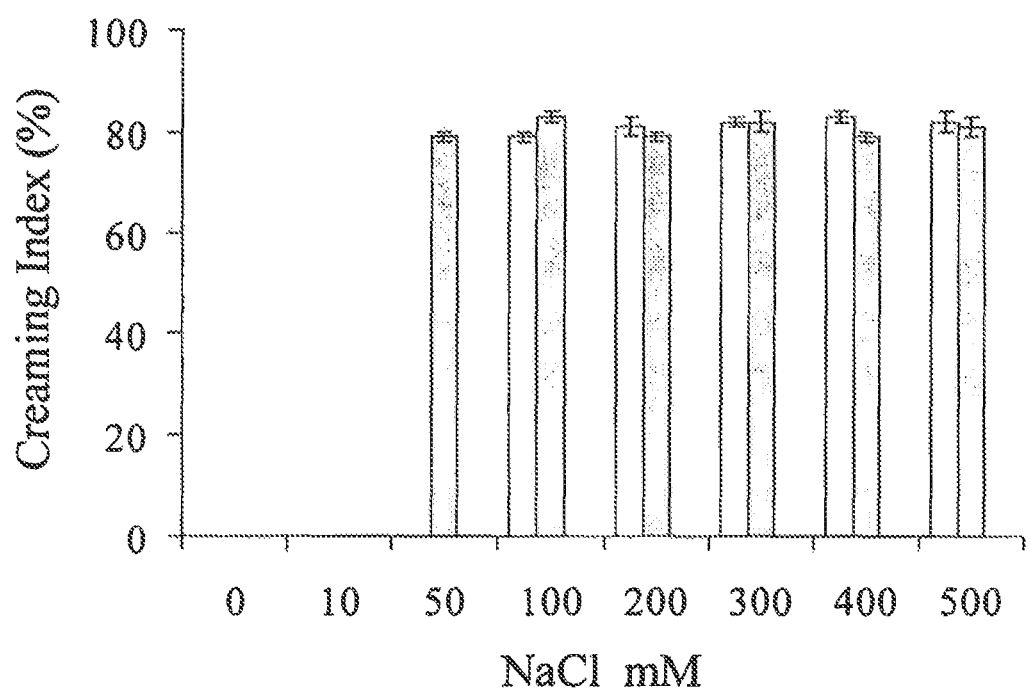

FIGS. 7A-C. Influence of NaCl concentration on (A) the $\zeta$-potential, (B) the mean particle diameter ($d_{32}$) and (C) the creaming stability of primary and secondary emulsions in the absence (0 AU) and presence (5 AU) of laccase at pH 7. The primary emulsions were prepared and kept at pH 7.0, while the secondary emulsions were prepared at pH 7.0, adjusted to pH 4.5, then brought back to pH 7.0.

DETAILED DESCRIPTION OF CERTAIN EMBODIMENTS

Illustrating other embodiments of this invention, an electrostatic deposition method described previously was used to prepare emulsions containing lipid droplets coated by β-lactoglobulin-pectin layers. Representative of other embodiments, bovine β-Lactoglobulin (β-Lg) was selected as an emulsifier to form the primary adsorbed layer around the lipid droplets because it is a surface-active globular protein with well known molecular and functional characteristics. Likewise, representative of other embodiments, pectin was selected as a polysaccharide to form the secondary adsorbed layer because it is an anionic biopolymer that has previously been shown to adsorb to β-Lg-coated droplets at pH values below the isoelectric point of such proteins. Beet pectin was used in this study because it can be covalently cross-linked by an enzyme (laccase). Beet pectin is extracted from sugar beet pulp, which is a by-product of the sugar industry. Unlike citrus pectins, beet pectins have ferulic acid groups esterified to some of the neutral sugars in the side-chains of the so-called "hairy" regions. Oxidative enzymes, such as laccase and peroxidase, can oxidise these ferulic acid groups through a free radical mechanism resulting in the formation of covalent cross-links between beet pectin molecules. Studies have shown that laccase can also cross-link whey proteins in the presence of phenolic acids. Therefore, laccase can be used to initiate protein-protein cross-links in the primary interfacial layer, polysaccharide-polysaccharide cross-links in the secondary interfacial layer, and/or protein-polysaccharide cross-links between layers.

As demonstrated, below, stable emulsions containing lipid droplets coated by β-lactoglobulin and beet pectin can be formed, with the beet pectin layer covalently cross-linked by laccase. Illustrating broader application of this invention, such emulsions have improved stability over primary emulsions or secondary emulsions with no cross-linking. Mimicking biochemical processes prevalent in nature (such as enzymatic cross-linking of pectin) allows rational design of novel functional performance into commercial emulsified products (e.g., food products, etc.).

With reference to the following examples, laccase was used to crosslink the beet pectin molecules, and to ascertain the amount of such an enzyme needed for adequate cross-linking within a certain timescale. The ability of laccase to crosslink the pectin molecules was established using UV-visible absorption and gelation measurements.

At pH 4.5, there was no evidence of a peak in the absorption spectrum of citrus pectin from 200 to 800 nm, but there was an appreciable peak around 320 to 330 nm in the absorption spectrum of the beet pectin (FIG. 1). Previous studies have attributed this peak to absorption by ferulic acid groups. The difference in the absorption spectra of citrus and beet pectins can therefore be attributed to the greater amount of ferulic acid groups present in the latter. The height of the absorption peak due to the ferulic acid groups changed when they were cross-linked by laccase. Consequently, measurements of the absorption of pectin solutions at 325 nm ($A_{325nm}$) were used to monitor the kinetics of ferulic acid cross-linking by laccase at 25° C. The data is presented as the normalized absorbance (A(t)/A(0)), i.e., the absorbance at time t divided by the initial absorbance at time 0 (FIG. 2). The UV-visible absorption spectra of 0.5 wt % beet pectin solutions were found to be similar at pH 4.5 and 7.0 (data not shown).

The beet pectin (0.1 wt %, pH 4.5) solutions initially had a relatively high absorbance at 325 nm (0.84 cm$^{-1}$). In the absence of laccase, the absorbance of the beet pectin solutions did not change significantly over time (FIG. 2A). When laccase was added to the beet pectin solutions the absorbance decreased over time, which was attributed to cross-linking of the ferulic acid groups catalyzed by the enzyme. The absorbance decreased steeply during the first 250 to 2500 seconds (depending on laccase concentration) and then decreased more gradually. The initial slope in the relative absorbance with time (1/A(0)×dA(t)/dt) increased with increasing laccase concentration (FIG. 2B). There was not a large change in the reaction rate between 5 and 10 AU, so we used 5 AU for the remainder of the experiments. At pH 7, the beet pectin solutions containing 5 AU laccase had a fairly similar initial absorbance at 325 nm (0.79 cm$^{-1}$), but the decrease in relative absorbance with time was much less than at pH 5: $-0.16 \times 10^{-3}$ s$^{-1}$. This affect can be attributed to the fact that the optimum activity of laccase is around pH 2.5 to 5.5.

Additional information about the ability of laccase to crosslink beet pectin was obtained from gelation measurements. The influence of laccase (1 to 10 AU) on the gelation of 0.5 wt % citrus and beet pectin solutions was ascertained by visual observation. No gelation was observed in the citrus pectin samples, even after a few days of storage, although a gradual increase in solution viscosity was observed during storage. On the other hand, gelation was observed in the beet pectin samples within 2 hours of storage, with the gelation time decreasing with increasing laccase concentration: 105, 90, 60 and 50 minutes for 1, 2, 5 and 10 AU, respectively. These results support the UV-visible measurements, indicating that there were sufficient ferulic acid groups present in the beet pectin to promote extensive cross-linking of the polysaccharide molecules, but that there was much less ferulic acid in the citrus pectin.

The purpose of these experiments was to establish the optimum beet pectin concentration required to form stable secondary emulsions containing β-Lg-pectin coated droplets. The electrical charge (ζ-potential) and mean particle diameter ($d_{32}$) of emulsions (1 wt % corn oil, 0.05 wt % β-Lg, 5 mM phosphate buffer, pH 4.5) containing different beet pectin concentrations (0 to 0.2 wt %) were measured 24 hours after preparation (FIGS. 3 and 4). In the absence of pectin, the electrical charge on the emulsion droplets was slightly positive (+7 mV) at pH 4.5 because the adsorbed β-Lg was below its isoelectric point (pI≈5). The electrical charge on the droplets changed from positive to negative as the pectin concentration in the emulsions was increased (FIG. 3). The negative charge on the droplets reached a relatively constant value (≈−31 mV) when the pectin concentration exceeded about 0.04 wt %. These measurements indicated that negatively charged pectin molecules adsorbed to the surface of the β-Lg coated lipid droplets until the droplets became saturated with polysaccharide.

The stability of the secondary emulsions was determined by static light scattering, microscopy and creaming measurements (FIG. 4). The mean particle diameter was relatively high ($d_{32}$>10 μm), large aggregates were observed in the photo-micrographs (d>10 μm), and rapid creaming (CI>70%) was observed in the emulsions containing 0 and 0.01 wt % beet pectin. These results can be attributed to the low droplet charge and/or extensive bridging flocculation of the cationic protein-coated droplets by the anionic polysaccharide molecules. At pectin concentrations higher than 0.02 wt % the emulsions appeared relatively stable to droplet aggregation ($d_{32}$<1 μm; no visible flocs; CI≈0%). These latter results suggest that there was sufficient pectin present to rapidly adsorb and fully cover the protein-coated lipid droplet surfaces thereby preventing bridging flocculation, but there was not so much non-adsorbed pectin remaining in the aqueous phase that it caused depletion flocculation. For these reasons, 0.04 wt % beet pectin was used in the remainder of the studies to form stable lipid droplets coated by a protein-polysaccharide interfacial complex.

Studies were conducted to examine the impact of laccase catalyzed cross-linking of the adsorbed pectin molecules on the stability of the secondary emulsions. A series of secondary emulsions were prepared containing either 0 or 5 AU of laccase (Section 2.4.2). The particle charge and mean particle diameter of the emulsions were then measured at pH 7.0 (initial), pH 4.5 (laccase treatment) and pH 7.0 (final) (FIGS. 5 and 6).

The protein-coated lipid droplets in the initial primary emulsion had a relatively high negative charge ($\zeta=-76$ mV) at pH 7.0 because this pH was above the isoelectric point (pI) of the adsorbed $\beta$-Lg (pI$\approx$5). In addition, the mean particle size was relatively small (z-average diameter=0.21 μm), which indicated that the initial primary emulsion was stable to droplet aggregation. When the primary emulsion was adjusted to pH 4.5 the droplets became positively charged ($\zeta\approx+2$ mV) because this pH was slightly below the pI of $\beta$-Lg (FIG. 5). In addition, extensive droplet flocculation occurred at this pH (z-average diameter>6 μm), which can be attributed to the reduction of the electrostatic repulsion between the droplets (FIG. 6). When the primary emulsion was adjusted back to pH 7.0 the protein-coated lipid droplets again became negatively charged ($\zeta=-55$ mV), although the charge was appreciably less negative than in the initial emulsion at pH 7.0 ($\zeta=-76$ mV). This reduction in the magnitude of the charge can be attributed to the increase in ionic strength associated with adding HCl and NaOH to adjust the pH from 7.0 to 4.5 to 7.0. The droplets in the primary emulsion remained highly aggregated (z-average diameter=3.2 μm) after the pH was adjusted from pH 4.5 to pH 7.0, which indicates that the droplet aggregation that occurred at pH 4.5 was at least partially irreversible.

The droplets in the secondary emulsions were highly negatively charged at pH 4.5 (in contrast to those in the primary emulsions), which indicated that anionic pectin molecules adsorbed to positive patches on the protein-coated lipid droplets (FIG. 5). The pectin molecules adsorb to the protein-coated droplet surfaces when the pH is decreased from 7 to 4.5 due to electrostatic attraction between the anionic pectin and cationic patches on the protein surface. The addition of laccase caused no significant change (p<0.05) in the $\zeta$-potential of the droplets in the emulsions. All of the secondary emulsions (0 and 5 AU laccase) were stable to extensive droplet aggregation at pH 4.5, with the z-average diameter being $\approx$0.35 μm. These results suggest that the adsorption of the pectin molecules to the droplet surfaces stabilized them against flocculation, which can be attributed to their ability to increase the electrostatic and steric repulsion between the droplets, and reduce the van der Waals attraction. The fact that the measured mean particle diameter was larger in the secondary emulsions at pH 4.5 than in the primary emulsions at pH 7.0 can be attributed to the presence of the adsorbed polysaccharide layer around the protein-coated droplets or to some droplet aggregation occurring during pH adjustment. When the secondary emulsions were adjusted from pH 4.5 to pH 7.0 the particles became highly negatively charged (FIG. 5) and they remained relatively small (FIG. 6), which suggested that they were stable to extensive droplet aggregation. Unfortunately, the $\zeta$-potential measurements at pH 7.0 did not enable ascertaining whether the beet pectin molecules remained attached to the droplet surfaces (as would be expected for cross-linked pectin), or whether they became detached (as would be expected for non-cross-linked pectin). Such results indicate that beet pectin did adsorb to the protein-coated lipid droplets at pH 4.5 and stabilize them against aggregation.

It was hypothesized that beet pectin that was covalently cross-linked at the droplet surfaces would remain attached when the pH was adjusted from pH 4.5 to pH 7.0, but pectin that was not covalently cross-linked would become detached because of the electrostatic repulsion between the anionic $\beta$-Lg and pectin molecules. If the pectin layer did remain attached to the droplet surfaces at pH 7, then the emulsions would be expected to be more stable to salt because there would be a strong steric repulsion between them and a weaker van der Waals attraction. Studies were conducted to examine the influence of salt (NaCl and $CaCl_2$) on the stability of primary and secondary emulsions (0 or 5 AU laccase) at pH 7.0.

The influence of NaCl concentration (0 to 500 mM) on the $\zeta$-potential, mean particle diameter, and creaming stability of primary and secondary emulsions at pH 7.0 was measured (FIG. 7A). In this series of experiments the primary emulsion was prepared and kept at pH 7.0 (to avoid aggregation at the isoelectric point), but the secondary emulsions were prepared at pH 7.0, adjusted to pH 4.5, then brought back to pH 7.0. The $\xi$-potential in the primary and secondary emulsions was negative at all ionic strengths, but the magnitude of the $\zeta$-potential decreased as the NaCl concentration increased, which can be attributed to electrostatic screening. The mean particle diameter ($d_{32}$) of the primary emulsions increased appreciably when they contained ≥300 mM NaCl (FIG. 7B). However, appreciable creaming instability was observed in the primary emulsions at ≥100 mM NaCl (FIG. 7C). The difference in the minimum salt concentration required to promote emulsion instability between the particle size and creaming measurements can be attributed to the fact that the emulsions had to be diluted appreciably for the light scattering measurements, which may have disrupted any weak flocs present.

Interestingly, the secondary emulsions containing no enzyme (0 AU laccase) were less stable than the primary emulsions, exhibiting an appreciable increase in mean particle diameter and creaming instability at ≥50 mM NaCl. This effect can be attributed to the fact that there is free (non-adsorbed) pectin present in these secondary emulsions at pH 7.0, which will generate a depletion attraction between the droplets. Hence, the height of the repulsive energy barrier between the droplets will be lower than in the absence of pectin, which would mean that less salt was required to induce aggregation. On the other hand, the secondary emulsions containing enzyme (5 AU laccase) were much more stable to aggregation than the primary emulsions, showing no change in mean particle diameter and no creaming from 0 to 500 mM NaCl (FIG. 7). It is postulated that the adsorbed beet pectin was cross-linked by laccase at pH 4.5, which prevented it from desorbing from the droplet surfaces when the pH was adjusted to pH 7.0. Consequently, there was a thick polymer layer around the lipid droplets, which increased the steric repulsion and reduced the van der Waals attraction between the droplets, thereby increasing their stability.

Similar experiments were carried out using $CaCl_2$ (0 to 200 mM) rather than NaCl (data not shown). It was found that the primary emulsion and the secondary emulsion without laccase treatment were stable from 0 to 5 mM $CaCl_2$, but were unstable to droplet aggregation and creaming at ≥8 mM $CaCl_2$. On the other hand, the secondary emulsion containing laccase was stable from 0 to 8 mM $CaCl_2$, but unstable at ≥10 mM $CaCl_2$. The reason that a much lower concentration of $CaCl_2$ was required to promote droplet aggregation than NaCl is because the counter-ion was divalent ($Ca^{2+}$), rather than monovalent ($Na^+$). Multivalent counter-ions are much more effective at promoting droplet aggregation than monovalent ions for a number of reasons: (i) they increase the ionic strength more effectively, thereby causing greater electrostatic screening; (ii) they bind to oppositely charged droplet surfaces, thereby reducing their charge density; (iii) they can act as "salt-bridges" between oppositely charged droplets. These results showed that covalently cross-linking pectin with laccase provided some degree of protection against droplet aggregation in the presence of calcium ions, but was much less effective than for sodium ions. It is well known that calcium ions can crosslink pectin molecules in aqueous solutions, and therefore it is not surprising that calcium ions were able to promote droplet flocculation in the secondary emulsions.

EXAMPLES OF THE INVENTION

The following non-limiting examples and data illustrate various aspects and features relating to the compositions and/or methods of the present invention, including the interfacial assembly of oil in water emulsion systems, as are available through the methodologies described herein. In comparison with the prior art, the present compositions and methods provide results and data that are surprising, unexpected and contrary thereto. While the utility of this invention is illustrated through the use of several emulsions, hydrophobic phases, components and cross-linking agents that can be used therewith, it will be understood by those skilled in the art that comparable results are obtainable with various other emulsion systems, phases, components and/or cross-linking agents, as are commensurate with the scope of this invention.

Materials

Powdered β-lactoglobulin (β-Lg) was kindly supplied by Davisco Foods International (lot no. JE 003-3-922, Le Sueur, Minn.). The protein content was reported to be 98.3% (dry basis) by the supplier, with β-g making up 95.5% of the total protein. The moisture content of the protein powder was reported to be 4.9%. Beet pectin was obtained from Herbstreith & Fox K G (Elmsford, N.Y.) and citrus pectin was purchased from Sigma-Aldrich Co. (St Louis, Mo.). As stated by the manufacturers, the degree of esterification (DE) of the citrus pectin and beet pectin were respectively 60% and 50%. laccase enzyme (from *Trametes versicolor*) was purchased from Sigma-Aldrich Co. (lot no. 1210197 10306259, Steinheim, Germany). Laccase was reported to have 22.6 activity units per mg (AU) of enzyme. Corn oil was purchased from a local supermarket and used without further purification. Analytical grade hydrochloric acid, sodium hydroxide, sodium azide, and sodium phosphate were obtained from Sigma-Aldrich (St. Louis, Mo.). Distilled and de-ionized water was used for the preparation of all solutions.

Example 1

Solution Preparation

Stock buffer solutions were prepared by dispersing 5 mM disodium hydrogen phosphate in distilled water and then adjusting the pH to either 4.5 or 7.0 using 1 M HCl and/or 1 M NaOH. Citrus pectin and beet pectin solutions were prepared by dispersing 1 wt % powdered pectin into buffer solutions at pH 7.0. An emulsifier solution was prepared by dispersing 0.5 wt % β-lactoglobulin powder into buffer solution at pH 7.0. Enzyme solutions were prepared by dispersing 0.5 wt % laccase powder into buffer solutions (pH 4.5 and 7.0). A sodium azide solution (an antimicrobial) was prepared by dispersing 0.04 wt % of its powder into buffer solution (pH 7.0). Each solution was then stirred for at least two hours to ensure complete dissolution of the materials.

Example 2

Characterisation of Laccase Activity

Establishment of Laccase Activity: UV-Visible Measurements.

Information about the ability of laccase to cross-link pectin molecules was obtained from UV-visible absorption measurements (UV-2101 PC, Shimadzu Corporation, Japan). Initially, absorption spectra of 0.1 wt % pectin (beet and citrus) dissolved in aqueous phosphate buffer solutions were measured at pH 4.5 and pH 7.0, using buffer solutions containing no pectin as blanks. A maximum in the absorption spectrum was observed at a wavelength of 325 nm for beet pectin, which was attributed to the presence of the ferulic acid groups. Consequently, absorption measurements at this wavelength ($A_{325nm}$) were used to establish the ability of laccase to cross-link the pectin. Different amounts of laccase (0 to 10 AU) were added to samples of beet pectin (0.1 wt %) at pH 4.5. The oxidation of ferulic acid was then followed by measuring the absorbance at 325 nm at 25° C. for one and a half hours.

Example 3

Establishment of Laccase Activity

Pectin Gelation.

A qualitative indication of the ability of laccase to cross-link pectin molecules was obtained by examining the enzymes influence on the gelling properties of polysaccharide solutions. Solutions of citrus and beet pectin (0.5 wt %) were prepared in stock buffer solution at pH 4.5, then different amounts of laccase were added (0 to 10 AU) and the resulting solution was stirred for 30 minutes. The gelation state of the system was determined by visual inspection of the reaction mixture. Periodically, the vessel containing the reaction mixture was tilted and the system was considered to have gelled when it did not deform under its own weight. The "gelation time" was then defined as the time required for a self-supporting gel to be formed.

The above experiments indicated that 5 AU of laccase were sufficient to promote cross-linking of the ferulic acid (see above): this amount was used in subsequent experiments.

Example 4

Emulsion Preparation

Optimum Conditions to Form Protein-Polysaccharide Coated Droplets

Preliminary experiments were carried out to determine the optimum beet pectin concentration required to create secondary emulsions. Primary emulsions were prepared by homogenizing 10 wt % corn oil with 90 wt % aqueous emulsifier solution (0.5 wt % β-lactoglobulin in distilled water, pH 7.0) in a high-speed blender (M133/1281-0, Biospec Products, Inc., ESGC, Switzerland) followed by five passes at 3000 psi through a high-pressure valve homogenizer (LAB 1000, APV-Gaulin, Wilmington, Mass.). The primary emulsion was then heated to 80° C. for 20 minutes to covalently cross-link the adsorbed β-lactoglobulin molecules, thereby avoiding the possibility of any surface-active components in the beet pectin ingredient displacing the protein from the oil-water interface. The droplets did not aggregate during this process because at low ionic strengths there is a strong electrostatic repulsion between them.

Secondary emulsions were formed by mixing primary emulsions with aqueous beet pectin solutions at pH 7.0 for 10 minutes using a magnetic stirrer to produce a series of emulsions with different pectin concentrations: 1 wt % corn oil, 0.05 wt % β-Lg, and 0 to 0.2 wt % beet pectin. The pH was then adjusted to pH 4.5 with 1 M HCl and the emulsions were stirred for 20 minutes using a magnetic stirrer. The resulting emulsions were then stored at room temperature for 24 h before being analyzed. The ζ-potential, particle size distribution and creaming stability of the emulsions were then measured (see below). The optimum beet pectin concentration required to form non-aggregated lipid droplets coated by pectin was determined to be 0.04 wt % (see below), so that this amount was used to prepare the secondary emulsions in all subsequent experiments.

Example 5

Influence of Laccase on the Stability of Secondary Emulsions

A purpose of these experiments was to study the impact of laccase catalyzed cross-linking of the adsorbed pectin molecules on the stability and properties of secondary emulsions. The present methodologies were used to prepare secondary emulsions containing 1 wt % corn oil, 0.05 wt % cross-linked β-Lg and either 0 or 0.04 wt % pectin (5 mM phosphate buffer, pH 7.0). These emulsions were then adjusted to pH 4.5 using 1 M HCl, and then either 0 or 5 AU laccase was added. The emulsions were then stored for 24 hours at ambient temperature prior to analysis. A series of emulsions were prepared using this approach to study the influence of pectin and laccase on their properties: (i) "control"—0 wt % pectin, 0 AU laccase; (ii) "beet (0 AU)"—0.04 wt % beet pectin, 0 AU laccase; and (iii) "beet (5 AU)"—0.04 wt % beet pectin, 5 AU laccase.

Example 6

Salt Stability of Emulsions

The influence of salt addition on the stability of the primary and secondary emulsions was examined at pH 7. Primary emulsions (0 wt % pectin) and secondary emulsions (0.04 wt % beet pectin) were prepared at pH 7.0. The emulsions were then adjusted to pH 4.5 using 1M HCl and either 0 or 5 AU of laccase were added. After 24 hours storage at ambient temperature, the emulsions were adjusted to pH 7.0 with 1M NaOH. NaCl (0 to 500 mM) or $CaCl_2$ (0 to 200 mM) was then added to the emulsions and they were stored for a further 24 hours at room temperature prior to analysis.

Example 7

Particle Size Measurements

The particle size distribution of the emulsions was measured using both static light scattering (Mastersizer MSS, Malvern Instruments, Worcestershire, UK) and dynamic light scattering (Zetasizer Nano-ZS, Malvern Instruments, Worcs., UK). For both techniques, the emulsions were diluted prior to analysis using an appropriate phosphate buffer solution to avoid multiple scattering effects. The mean particle size was reported as the surface-weighted mean diameter ($d_{32}=\Sigma n_i d_i^3 / \Sigma n_i d_i^2$) for the static light scattering measurements, and the intensity-weighted mean diameter (z-average) for the dynamic light scattering measurements. The static light scattering measurements were mainly used for highly flocculated emulsions containing large particles (d>10 μm), whereas the dynamic light scattering was mainly used for non-flocculated emulsions containing small particles (d<1 μm).

Example 8

ξ-Potential Measurements

Emulsions were diluted to a droplet concentration of approximately 0.005 wt % using an appropriate buffer solution to avoid multiple scattering effects. Diluted emulsions were injected directly into the measurement chamber of a particle electrophoresis instrument (ZEM5002, Zetamaster, Malvern Instruments, Worcestershire, UK) that measured the direction and velocity of particle movement in the applied electric field. An individual ξ-potential measurement was determined from the average of five readings taken on the same sample.

Example 9

Optical Microscopy

Emulsions were gently agitated in a glass test tube before analysis to ensure that they were homogenous. A drop of emulsion was then placed on a microscope slide and covered with a cover slip. The microstructure of the emulsion was then observed using conventional optical microscopy (Nikon microscope Eclipse E400, Nikon Corporation, Japan). The images were acquired using a CCD camera (CCD-300T-RC, DAGE-MTI, Michigan City, Ind.) connected to Digital Image Processing Software (Micro Video Instruments Inc., Avon, Mass.) installed on a computer.

Example 10

Creaming Stability Measurement

Ten grams of emulsion were transferred into a test tube (internal diameter 15 mm, height 125 mm), tightly sealed with a plastic cap, and then stored for 1 day at room temperature. After storage, emulsions separated into an optically opaque 'cream' layer at the top and a transparent (or turbid) 'serum' layer at the bottom. As defined, the serum layer is the sum of the turbid and transparent layers. The total height of the emulsions ($H_E$) and the height of the serum layer (Hs) were measured. The extent of creaming was characterized by creaming index (%)=100×($H_S/H_E$). The creaming index provided indirect information about the extent of droplet aggregation in an emulsion: the faster the creaming, the larger the particle size.

Example 11

Statistical Analysis

Experiments were performed at least twice using freshly prepared samples. Averages and standard deviations were calculated from these measurements.

Demonstrating various aspects of this invention, the preceding examples show that laccase can be used to covalently cross-link beet pectin molecules adsorbed to the surfaces of protein-coated lipid droplets at pH 4.5. Results show that the beet pectin layer remains attached to the droplet surfaces when the pH is raised from 4.5 to 7.0 (e.g., as the composition is partially neutralized or neutralized), even though it would normally be expected to become detached because of the electrostatic repulsion between the anionic pectin and anionic protein-coated droplets at pH 7. Emulsions containing lipid droplets coated by β-lactoglobulin and cross-linked beet pectin had much better stability to salt (NaCl) than those coated by β-lactoglobulin alone, which can be attributed to the ability of the adsorbed pectin layer to increase the repulsive interactions and decrease the attractive interactions between the droplets. These results show that emulsions with improved functional performance can be prepared via a biomimetic approach, utilizing enzymes to cross-link adsorbed biopolymers.

While various principles relating to this invention have been described in conjunction with certain embodiments, it should be understood clearly that these descriptions are presented only by way of example and are not intended to limit, in any way, the scope of this invention. For instance, as would be understood by those skilled in the art made aware of this invention, the various methods and compositions of the present invention can also be directed to use of biopolymers such as agar, carrageenan, chitosan, and gelatin which can be cross-linked with genipin. Various proteins and carbohydrates can also be cross-linked by heating in conjunction with the Maillard reaction, after emulsion formation and corresponding biopolymer contact. Likewise, certain proteins, as would be understood by those skilled in the art, can be cross-linked with various other enzymes, including but not limited to a transglutaminase, by heating, or by introduction of certain other cross-linking compounds or reagents, such as but not limited to gluteraldehyde. Various other features and advantages of the present invention will become apparent from the claims hereinafter, as would be understood by those skilled in the art.

We claim:

1. A biomimetic method of using a cross-linkable biopolymer to prepare a stabilized emulsion composition, said method comprising:
    encompassing each droplet of a hydrophobic component with an emulsifier component; the hydrophobic component being formed into droplets and being in an aqueous medium; and
    adsorbing a biopolymer component on said emulsifier component that encompasses each droplet of the hydrophobic component; the biopolymer component comprising an intra-component covalent cross-linkage, said cross-linkage the reaction product of two cross-linkable moieties and a cross-linking reagent;
    at least a portion of said emulsifier component comprising a net charge and at least a portion of said biopolymer component comprising another net charge opposite the net charge of said emulsifier component, said emulsifier component and said biopolymer component being electrostatically interactive.

2. The method of claim 1 wherein said cross-linking agent is selected from heat, pH, a redox reagent and an enzyme.

3. The method of claim 1 wherein said biopolymer component is selected from pectins comprising ferulic acid moieties, proteins comprising phenolic acid moieties and combinations thereof.

4. The method of claim 3 wherein said biopolymer component is a beet pectin.

5. The method of claim 3 wherein said biopolymer moieties are cross-linked with an enzyme.

6. The method of claim 5 wherein said biopolymer is a beet pectin.

7. The method of claim 1 wherein said emulsifier component is a protein component comprising a net positive charge, said composition at a pH below the isoelectric point of said protein.

8. The method of claim 7 wherein said biopolymer component is a polysaccharide comprising a net negative charge.

9. The method of claim 8 wherein said emulsifier component is a whey protein comprising phenolic acid moieties, and said biopolymer component is a pectin comprising ferulic acid moieties; and said cross-linking agent is selected from a laccase enzyme, a peroxidase enzyme and combinations of said enzymes, to provide covalent intra-component cross-linkages, covalent inter-component cross-linkages and combinations thereof.

10. The method of claim 1 comprising adjusting pH of said composition to at least partially neutralize the net charge of at least one said component.

11. The method of claim 1 comprising alternating contact of said emulsifier and biopolymer components.

12. The method of claim 1 wherein said hydrophobic component is selected from at least one of fatty acids, poly-unsaturated fatty acids, triglycerides and functional derivatives thereof, carotenoids, terpenes, anti-oxidants, colorants, flavor oils, food oils, fat-soluble vitamins, nutrients, nutraceuticals and combinations thereof.

13. The method of claim 1 comprising incorporation of the emulsion composition into one of a food product, a beverage, a nutraceutical product, a cosmetic product and a pharmaceutical product.

14. A method for emulsion preparation, said method comprising:
    providing a lipid-protein emulsification product comprising a lipid component and a protein component; the lipid component being formed into a number of droplet; the protein component encompassing each droplet of the lipid component; and
    adsorbing a polysaccharide biopolymer component on the protein component that encompasses each droplet of the lipid component; the polysaccharide biopolymer component comprising an intra-component covalent cross-linkage, said cross-linkage the reaction product of two cross-linkable moieties and a cross-linking reagent.

15. The method of claim 14 wherein said polysaccharide biopolymer component is selected from pectins comprising ferulic acid moieties and combinations thereof, said polysaccharide biopolymer component cross-linked with an enzyme.

16. The method of claim 15 wherein said polysaccharide biopolymer component is a beet pectin.

17. The method of claim 14 wherein said emulsifier component is selected from dairy proteins and combinations thereof.

18. The method of claim 17 wherein said emulsifier component is a whey protein comprising phenolic acid moieties, and said polysaccharide biopolymer component is a pectin comprising ferulic acid moieties; and said cross-linking agent is selected from a laccase enzyme, a peroxidase enzyme and combinations of said enzymes, to provide covalent intra-component cross-linkages, covalent inter-component cross-linkages and combinations thereof.

19. The method of claim 14 wherein said lipid component is selected from at least one of fatty acids, poly-unsaturated fatty acids, triglycerides and functional derivatives thereof, carotenoids, terpenes, anti-oxidants, colorants, flavor oils, food oils, fat-soluble vitamins, nutrients, nutraceuticals and combinations thereof, said emulsification product incorporated into one of a food product, a beverage, a nutraceutical product, a cosmetic product and a pharmaceutical product.

* * * * *

UNITED STATES PATENT AND TRADEMARK OFFICE
CERTIFICATE OF CORRECTION

PATENT NO. : 9,040,109 B2  
APPLICATION NO. : 14/085212  
DATED : May 26, 2015  
INVENTOR(S) : David Julian McClements et al.

Page 1 of 1

It is certified that error appears in the above-identified patent and that said Letters Patent is hereby corrected as shown below:

In the claims

In column 16, line 40 (claim 14), "a number of droplet;" should read -- a number of droplets; --

Signed and Sealed this
Twentieth Day of October, 2015

Michelle K. Lee
*Director of the United States Patent and Trademark Office*